| United States Patent [19] | [11] Patent Number: 4,885,243 |
| Huber et al. | [45] Date of Patent: Dec. 5, 1989 |

[54] PROCESS FOR PRODUCING A-21978C DERIVATIVES

[75] Inventors: Floyd M. Huber, Danville; Richard L. Pieper, Indianapolis; Anthony J. Tietz, Plainfield, all of Ind.

[73] Assignee: Eli Lilly and Company, Indianapolis, Ind.

[21] Appl. No.: 773,762

[22] Filed: Sep. 9, 1985

Related U.S. Application Data

[63] Continuation-in-part of Ser. No. 658,979, Oct. 9, 1984, abandoned.

[51] Int. Cl.$^4$ .................... C12P 21/04; C12R 1/465; C07K 1/00
[52] U.S. Cl. .................................. 435/71.3; 435/886; 530/317
[58] Field of Search .......................... 435/70, 71, 886; 530/317

[56] References Cited

U.S. PATENT DOCUMENTS

4,288,403  6/1980  Hamill et al. ..................... 424/115
4,331,594  5/1982  Hamill et al. ..................... 435/71
4,482,487  11/1984  Abbott et al. ..................... 530/317

*Primary Examiner*—Elizabeth C. Weimar
*Attorney, Agent, or Firm*—Nancy J. Harrison; Leroy Whitaker

[57] ABSTRACT

An improved process for producing A-21978C cyclic peptide derivatives having a $C_2$–$C_{14}$ alkanoyl side chain which comprises feeding a $C_2$–$C_{14}$ alkanoic acid, or an ester or salt thereof, to the A-21978C-producing culture during the production stages of the fermentation.

11 Claims, No Drawings

PROCESS FOR PRODUCING A-21978C DERIVATIVES

CROSS-REFERENCE TO RELATED APPLICATION

This application is a continuation-in-part of copending application Ser. No. 658,979, filed Oct. 9, 1984, now abandoned.

SUMMARY OF THE INVENTION

This invention relates to an improved process for preparing derivatives of the A-21978C cyclic peptide antibiotics which have the formula

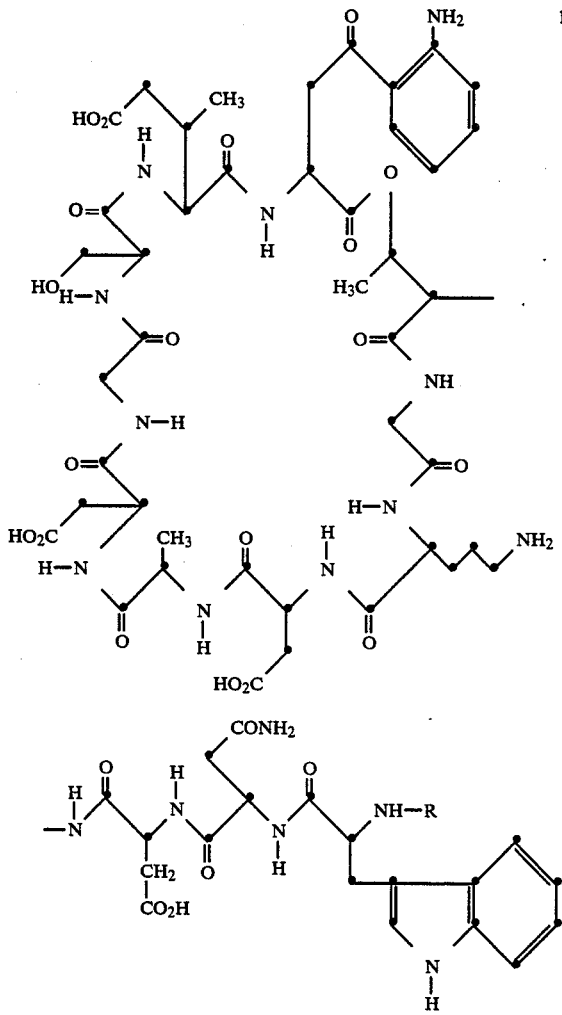

wherein R is $C_2$–$C_{14}$-alkanoyl. The improved process comprises feeding a $C_2$–$C_{14}$-alkanoic acid to the A-21978C producing culture during the fermentation. The advantages of this process are: (1) it requires fewer steps than the current process, (2) the product yield is increased; and (3) it requires less time.

DETAILED DESCRIPTION OF THE INVENTION

The A-21978C antibiotics are excellent antibacterial agents. A particularly important group of A-21978C derivatives are those having formula 1 (see Bernard J. Abbott, David S. Fukuda and Manuel Debono, U.S. Pat. No. 4,537,717, which will issue Aug. 27, 1985). Previously, preparation of these derivatives required a multistep process, which was time-consuming, yield-consuming and expensive. This invention provides an improved process for making these A-21978C derivatives directly. The prior process for preparing a formula 1 derivative, such as the n-decanoyl derivative of A-21978C, required the following steps:

1. Fermentation of the A-21978C-producing culture.
   a. Initiating with a liquid nitrogen ampoule.
   b. Primary inoculum stage (48 hours).
   c. Secondary inoculum stage (24 hours).
   d. Tertiary inoculum stage (24 hours).
   e. Fermentation (140 hours).
2. Filtration, resin adsorption and elution, and concentration.
3. Preparation of t-Boc complex.
4. Concentration of the complex.
5. Fermentation of the deacylating culture, e.g. *Actinoplanes utahensis*.
   a. Initiating with a liquid nitrogen ampoule
   b. Primary inoculum stage (72 hours)
   c. Secondary inoculum stage (48 hours)
   d. Fermentation (67 hours)
6. Deacylation of the complex with the deacylating culture.
7. Filtration, resin adsorption and elution, and concentration.
8. Reacylation.
9. Hydrolysis of the protecting group.
10. Final purification.

The novel process of this invention comprises adding a $C_2$–$C_{14}$ alkanoic acid (an ROH compound wherein R is as defined supra), or an ester or salt thereof, to an A-21978C-producing culture during the production stage of the fermentation (step 1e) to give the corresponding formula 1 compound. With this process, steps 3, 4, 5, 6, 7, 8 and 9 of the previous process can be eliminated. In addition, the new process substantially increases the yields obtained over those obtained using the previous process.

*Streptomyces roseosporus* strains NRRL 11379 and NRRL 15998, a mutant strain of NRRL 11379, are useful A-21978C-producing cultures. These cultures are part of the stock culture collection of the Northern Regional Research Center, U.S. Department of Agriculture, Agricultural Research Service, Peoria, Ill. 61604, from which they are available to the public under the accession numbers NRRL 11379 and NRRL 15998. The *S. roseosporus* NRRL 11379 culture and conditions for its use in the production of the A-21978C antibiotics are described by Robert L. Hamill and Marvin M. Hoehn in U.S. Pat. No. 4,331,594, incorporated herein by reference.

The naturally occurring A-21978C factors described in U.S. Pat. No. 4,331,594 are factors $C_0$, $C_1$, $C_2$, $C_3$, $C_4$ and $C_5$. In factors $C_1$, $C_2$, $C_3$, $C_4$ and $C_5$, the R in formula 1 is a specific $C_{10}$–$C_{12}$-alkanoyl group. A-21978C factor $C_0$, earlier thought to have a unique branched $C_{10}$-alkanoyl side chain, has been found to be a mixture of two components in approximately a 2:1 ratio. The major component has a branched-$C_{10}$-side chain, and the minor component has the straight-$C_{10}$-side chain.

For convenience in discussions herein when a formula 1 compound is prepared by the process of this invention, it is also called an A-21978C factor. Except for the naturally occurring factors, the length of the side chain is used to designate the factor. Thus, for example, the formula 1 compound wherein R=octanoyl, when prepared by this process is called an A-21978C$_8$ factor.

In the C$_2$-C$_{14}$ alkanoic acid, ester or salt (the substrate) used in the process of this invention, the alkyl portion can be a straight or branched chain. To prepare the naturally occurring A-21978C factors C$_1$, C$_2$ or C$_3$, for example, an 8-methyldecanoic, 10-methyldodecanoic or 10-methylundecanoic acid, ester or salt would be used. The C$_2$-C$_{14}$ straight-chain acids, esters and salts are recommended for use in the process because of their availability and lower cost. An especially preferred substrate is n-decanoic acid and its esters and salts.

When using a C$_2$-C$_{14}$ alkanoic acid ester, the C$_1$-C$_4$-alkyl esters are preferred. In such an ester, the C$_1$-C$_4$-alkyl group may also be straight or branched.

Representative suitable salts of C$_2$-C$_{14}$-alkanoic acids which may be used in the process include those formed from alkali metals and alkaline-earth metals such as sodium, potassium, lithium, cesium, rubidium, barium, calcium and magnesium. Suitable amine salts include the ammonium and the primary, secondary and tertiary C$_1$-C$_4$-alkyl- ammonium and hydroxy-C$_2$-C$_4$-alkylammonium salts.

It is preferable to add the substrate to the fermentation in the form of a sterile solution. A particularly useful solvent for this purpose is methyl oleate, although other solvents such as ethanol, ethyl acetate and C$_1$-C$_4$ esters of unsaturated fatty acids can be used. If the substrate is suitably fluid at the fermentation temperature, it may be added directly.

The rate of addition of the substrate to the fermentation must be low enough to avoid producing a toxic effect on the fermentation, but high enough to increase the yield of the desired formula 1 compound. Rates of addition of about 0.05 to about 0.5 ml per liter of fermentation broth per hour are recommended. A rate of from about 0.1 to about 0.2 ml per liter of fermentation broth per hour is preferred.

The substrate is added to the growing A-21978C-producing culture during the production stage of the fermentation, beginning at from about 15 to about 32 hours and continuing until the fermentation is terminated. The substrate can be added by various methods. It is preferable, however, to add it by a method which best approaches a steady flow.

Following the fermentation, the desired formula 1 compound, which is produced as an A-21978C factor (as defined, supra), can be recovered using procedures known in the art (see, e.g., U.S. Pat. No. 4,331,594).

The formula 1 compounds are excellent antibacterial agents.

In order to illustrate more fully the operation of this invention, the following examples are provided.

EXAMPLE 1

Production of the A-21978C Complex

A stock culture is prepared and maintained in the vapor phase of liquid nitrogen. *Streptomyces roseosporus* NRRL 15998 previously stored in the vapor phase of liquid nitrogen was used to inoculate 50 ml of vegetative medium of the following composition:

| Ingredient | Amount (%) |
| --- | --- |
| Trypticase Soy Broth* | 3.0 |

-continued

| Ingredient | Amount (%) |
| --- | --- |
| Dextrin | 2.5 |
| Water (deionized) | 94.5 |

*Baltimore Biological Laboratories, Cockeysville MD.

The inoculated medium was incubated in a 250-ml Erlenmeyer flask at 30° C. for 48 hours on a shaker rotating through an arc of two inches at 250 RPM. The mature vegetative culture was dispensed into multiple containers (0.5 ml/container) and stored in the vapour phase of liquid nitrogen.

In order to provide a larger uniform supply of stored material, one ml of the culture stored in liquid nitrogen was used to inoculate 80 ml of the vegetative medium described above. The inoculated vegetative medium was incubated in a 250-ml Erlenmeyer flask at 30° C. for 48 hours on a shaker rotating through an arc two inches in diameter at 250 RPM.

Ten ml of such a culture was used to inoculate 450 ml of a second-stage vegetative growth medium having the same composition as the primary vegetative medium described supra. The second-stage medium was incubated in a 2-liter Erlenmeyer flask for 24 hours at 30° C. on a shaker rotating through an arc of 2 inches at 250 RPM.

One liter of the second-stage vegetative culture was used to inoculate 39 liters of sterile tertiary inoculum development medium having the following composition:

| Ingredient | Amount (%) |
| --- | --- |
| Soybean Flour | 0.5 |
| Yeast Extract$^a$ | 0.5 |
| Calcium Gluconate | 1.0 |
| KCl$^b$ | 0.02 |
| MgSO$_4$ · 7H$_2$O$^b$ | 0.02 |
| FeSO$_4$ · 7H$_2$O$^b$ | 0.0004 |
| Sag 471 (antifoam)$^c$ | 0.03 |
| Water | 97.9296 |

$^a$Difco Laboratories, Detroit MI
$^b$Trace minerals were prepared as follows: FeSO$_4$ · 7H$_2$O (7.6 g) was dissolved in conc. HCl (76 ml). MgSO$_4$ · 7H$_2$O (380 g), KCl (380 g) and deionized water were added to bring the total volume to 3800 ml. To provide the specified minerals, use 80 ml of solution per 39 liters of tertiary inoculum development stage.
$^c$Union Carbide, Danbury CT.

The inoculated medium was incubated 24 hours in a stainless steel vessel at 30° C. The vessel was aerated with sterile air at 0.85 v/v/m and stirred with conventional agitators at 350–450 RPM. The pressure on the vessel was maintained at 5 PSIG.

One liter of the incubated tertiary inoculum stage was used to inoculate 119 liters of sterile production medium having the following composition:

| Ingredient | Amount (%) |
| --- | --- |
| Soybean Flour | 2.2 |
| Fe(NH$_4$)$_2$SO$_4$ · 6H$_2$O | 0.066 |
| Dextrose | 0.825 |
| Sag 471 | 0.022 |
| Potato Dextrin | 3.3 |
| Molasses (blackstrap) | 0.275 |
| Tap Water | 93.312 |

The pH was adjusted to 7.0 after addition of the first two ingredients and again after addition of all the ingredients immediately prior to sterilization.

The inoculated production medium was incubated 6 days in a stainless steel vessel at 30° C. and aerated with sterile air at a rate of 0.5 v/v/m. The medium was stirred with conventional agitators at 250 RPM from 0 to 15 hours and at 350 RPM after 15 hours. The pH was maintained at or above 6.5 by addition of ammonium hydroxide solution. The yield of A-21978C complex was 0.282 grams per liter of broth at the end of the fermentation. The factor distribution is described in Table 1.

EXAMPLE 2

Enhanced Production of A-21978C$_8$

The primary, secondary, and the tertiary growth stages were carried out as described in Example 1. The production stage was initiated as described in Example 1 except, beginning at 28 hours a sterile solution consisting of 50% v/v caprylic (octanoic) acid and methyl oleate was fed to the fermentation at a rate of 0.13 ml per liter of fermentation broth per hour and maintained at this rate until termination of the fermentation at 144 hours. The yield of A-21978C complex was 1.255 grams per liter of broth, a 445% increase in yield over that in Example 1. Factor A-21978C$_8$ (the formula 1 compound wherein R=octanoyl) represented 9% of the total A-21978C complex prepared by this method; no A-21978C$_8$ was detected in A-21978C complex prepared by the method of Example 1.

EXAMPLE 3

Enhanced Production of A-21978C$_9$

The primary, secondary and tertiary inoculum development stages were carried out as described in Example 1. The production stage was initiated as described in Example 1 except, beginning at 28 hours, a sterile solution consisting of 25% v/v nonanoic acid, and 75% methyl oleate was fed to the fermentation at a rate of 0.13 ml per liter of fermentation broth per hour and maintained at this rate until termination of the fermentation at 144 hours. The yield of A-21978C complex was 0.821 grams per liter of broth, a 293% increase over that obtained in Example 1. Factor A-21978C$_9$ (formula 1: R=nonanoyl) represented 10% of the total A-21978C complex prepared by this method; no A-21978C$_9$ was detected in the A-21978C complex prepared by the method of Example 1.

EXAMPLE 4

Enhanced Production of A-21978C$_{10}$ Factor (formula 1: R=n-decanoyl)

The primary and second stage vegetative growth stages were cultured as described in Example 1. In the tertiary stage 800 ml of secondary inoculum culture were used to inoculate 950 liters of sterile tertiary inoculum development medium having the following composition:

| Ingredient | Amount (%) |
| --- | --- |
| Dextrose | 2.0 |
| Calcium Carbonate | 0.2 |
| Soybean Flour | 2.0 |
| Yeast Extract | 0.1 |
| KCl[a] | 0.02 |
| MgSO$_4$ · 7H$_2$O[a] | 0.02 |
| FeSO$_4$ · 7H$_2$O[a] | 0.0004 |
| Sag 471 (antifoam) | 0.02 |
| Water | 95.6396 |

[a]Trace mineral solution prepared as described in Example 1.

The inoculated medium was incubated 24 hours in a stainless steel vessel at 30° C. The vessel was aerated with sterile air at a rate of 0.8 v/v/m and stirred with conventional agitators. One liter of this tertiary stage inoculum was used to inoculate 119 liters of production stage medium having the composition described in Example 1. The production stage was also initiated as described in Example 1 except, beginning at 28 hours, a sterile solution consisting of 50% v/v capric (decanoic) acid and 50% methyl oleate was fed to the fermentation at a rate of 0.26 ml per liter of fermentation broth per hour and maintained at this rate until termination of the fermentation at 283 hours. The yield of A-21978C complex was 1.94 grams per liter of broth, a 687% increase over that obtained in Example 1. The concentration of the A-21978C$_{10}$ factor (formula 1: R=n-decanoyl) was 1.63 grams per liter or 84% of the total A-21978C complex. This was 13583% greater than the amount of A-21978C$_{10}$ produced using the Example 1 procedure.

EXAMPLE 5

Alternate Method of Enhanced Production of A-21978C$_{10}$

The primary, secondary, and tertiary inoculum development stages were carried out as described in Example 1. The production stage was initiated as described in Example 1 except, beginning at 28 hours, a sterile solution consisting of 25% v/v capric acid ethyl ester (ethyl caprate) and 75% methyl oleate was fed to the fermentation at a rate of 0.13 ml per liter of fermentation broth per hour and maintained at this rate until termination of the fermentation at 144 hours. The yield of A-21978C complex was 1.022 grams per liter, a 362% increase over that obtained in Example 1. The concentration of factor A-21978C$_{10}$ was 0.202 grams per liter or 20% of the total A-21978C complex. This was 1683% greater than the concentration of A-21978C$_{10}$ produced using the method of Example 1.

EXAMPLE 6

Alternate Method for Enhanced Production of A-21978C$_{10}$

The primary and second stage vegetative growth stages were cultured as described in Example 1. The tertiary stage inoculum was cultured as described in Example 4 except that the volume of medium was 1900 liters and the duration of the stage was extended to 48 hours. The aeration rate was 0.3 v/v/m from 0 to 24 hours, 0.45 v/v/m from 24 to 40 hours and 0.90 v/v/m from 40 to 48 hours. The production stage was initiated as described in Example 1. At 23 hours a sterile slurry of 0.004% yeast extract was batch fed to the fermentation. Beginning at 36 hours, a solution of glycerol and ammonium decanoate was fed at a rate of 0.84 ml per liter of fermentation broth per hour. The feeding solution contained glycerol (3600 g), deionized water (9000 ml), capric acid (1 liter), and concentrated ammonium hydroxide solution (620 ml). The feed was maintained at this rate until the fermentation was terminated at 143 hours. The yield of A-21978C complex was 1.772 grams per liter, a 628% increase over that obtained in Example 1. The concentration of factor A-21978C$_{10}$ was determined to be 0.739 grams per liter or 42% of the total A-21978C complex. This was 6158% greater than the concentration of A-21978C$_{10}$ when produced by the method of Example 1.

EXAMPLE 7

Enhanced Production of A-21978C$_{11}$

The primary, secondary, and tertiary inoculum stages were carried out as described in Example 1. The production stage was initiated as described in Example 1 except, beginning at 28 hours, a sterile solution consisting of 25% v/v undecanoic acid and 75% methyl oleate was fed to the fermentation at a rate of 0.13 ml per liter of fermentation broth per hour until termination of the fermentation at 144 hours. The yield of A-21978C complex was 1.62 grams per liter, a 574% increase over that obtained in Example 1. The concentration of factor A-21978C$_{11}$ (formula 1: R=undecanoyl) was determined to be 0.70 grams per liter or 43% of the total A-21978C complex. Factor A-21978C$_{11}$ could not be detected in the A-21978C complex prepared by the Example 1 method.

EXAMPLE 8

Enhanced Production of A-21978C$_5$

The primary, secondary, and tertiary inoculum stages were carried out as described in Example 1. The production stage was initiated as described in Example 1 except, beginning at 28 hours, a sterile solution consisting of 25% v/v lauric acid and 75% methyl oleate was fed to the fermentation at a rate of 0.13 ml per liter of fermentation broth per hour until termination of the fermentation at 144 hours. The yield of A21978C complex was 1.12 grams per liter, a 400% increase over that obtained in Example 1. The concentration of factor A-21978C$_5$ (formula 1: R=dodecanoyl) was determined to be 0.372 grams per liter or 33% of the total A-21978C complex. This was 5314% greater than the concentration of A-21978C$_5$ found in A-21978C complex produced by the method of Example 1.

EXAMPLE 10

Alternate Method for Enhanced A-21978C$_{10}$ Production

A-21978C$_{10}$ is produced using the method of Example 6, but the *Streptomyces roseosporus* NRRL 11379 culture is used.

We claim:

1. In the process for producing an A-21978C derivative of the formula

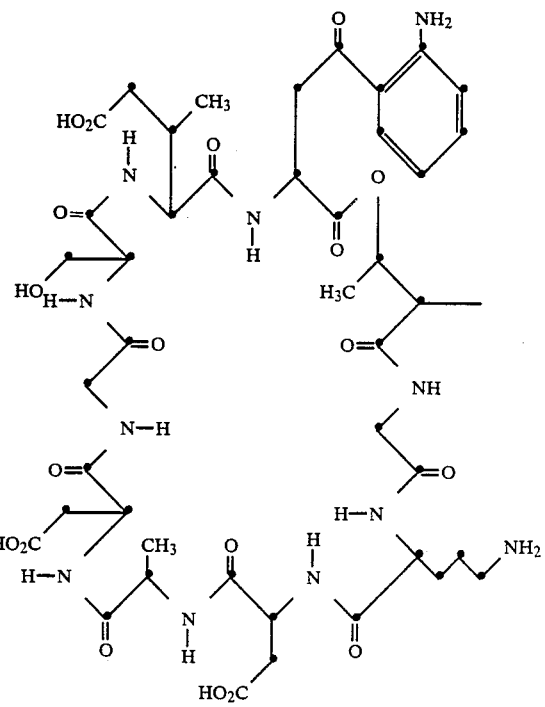

TABLE 1

EFFECT OF VARIOUS LIPID SUBSTRATES ON THE PRODUCTION of A-21978C COMPONENT

| | | A-21978C Component($\mu$g/ml)$^{a,b}$ | | | | | | | |
|---|---|---|---|---|---|---|---|---|---|
| Example | Lipid Substrate | C$_1$ | C$_2$ | C$_3$ | C$_5$ | C$_8$ | C$_9$ | C$_{10}$ | C$_{11}$ |
| 1 | None | 77 | 113 | 72 | 7 | — | — | 12$^c$ | — |
| 2 | Caprylic Acid | 276 | 312 | 214 | 175 | 113 | — | 170 | — |
| 3 | Nonanoic Acid | 147 | 177 | 125 | 192 | — | 83 | 90 | — |
| 4 | Capric Acid | 135 | 50 | 48 | 77 | — | — | 1630$^d$ | — |
| 5 | Capric Acid Ethyl Ester | 168 | 246 | 156 | 251 | — | — | 202$^d$ | — |
| 6 | Ammonium Decanoate | 335 | 371 | 228 | 98 | — | — | 739$^d$ | — |
| 7 | Undecanoic Acid | 163 | 206 | 158 | 273 | — | — | 118 | 700 |
| 8 | Lauric Acid | 204 | 236 | 141 | 372 | — | — | 173 | — |

$^a$The concentration of the antibiotic components in filtered broth was estimated by high performance liquid chromatography; the various components were detected by ultraviolet light absorption.
$^b$C$_0$, C$_1$, C$_2$, C$_3$ and C$_5$ = naturally occurring A-21978C factors; C$_8$, C$_9$, C$_{10}$ and C$_{11}$ = formula 1 compounds wherein R = C$_8$, C$_9$, C$_{10}$ and C$_{11}$ acryl groups, respectively.
$^c$Natural factor C$_0$
$^d$found to be substantially R = n-decanoyl

EXAMPLE 9

Alternate Production of the A-21978C Complex

A-21978C complex is produced using the procedure of Example 1, but the *Streptomyces roseosporus* NRRL 11379 culture is used.

-continued

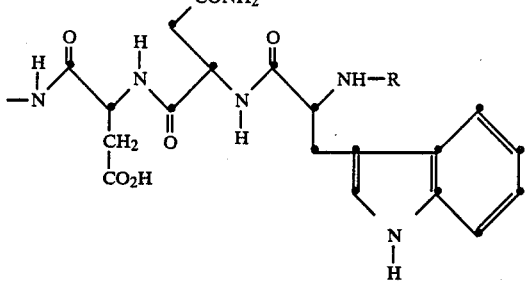

wherein R is a $C_2$–$C_{14}$-alkanoyl group, the improvement which comprises feeding the corresponding ROH acid, or an ester or salt thereof, to an A-21978C-producing *Streptomyces roseosporus* culture selected from NRRL 11379, NRRL 15998, or an A-21978C-producing mutant thereof, during the production stage of the fermentation until the A-21978C derivative is produced.

2. The process of claim 1 wherein a $C_2$–$C_{14}$-alkanoic acid is used.

3. The process of claim 1 wherein a $C_1$–$C_4$-alkyl ester of a $C_2$–$C_{14}$-alkanoic acid is used.

4. The process of claim 1 wherein a salt of a $C_2$–$C_{14}$-alkanoic acid is used.

5. The process of claim 2 wherein the alkanoic acid is caprylic acid.

6. The process of claim 2 wherein the alkanoic acid is nonanoic acid.

7. The process of claim 2 wherein capric acid is used.

8. The process of claim 3 wherein capric acid ethyl ester is used.

9. The process of claim 4 wherein ammonium decanoate is used.

10. The process of claim 2 wherein undecanoic acid is used.

11. The process of claim 2 wherein lauric acid is used.

* * * * *